(12) United States Patent
Vlasko-Vlasov et al.

(10) Patent No.: US 8,837,039 B2
(45) Date of Patent: Sep. 16, 2014

(54) MULTISCALE LIGHT AMPLIFICATION STRUCTURES FOR SURFACE ENHANCED RAMAN SPECTROSCOPY

(75) Inventors: Vitalii Vlasko-Vlasov, Downers Grove, IL (US); Aiqing Chen, Fremont, CA (US); Ulrich Welp, Lisle, IL (US); Stephen K Gray, Wheaton, IL (US)

(73) Assignee: Uchicago Argonne, LLC, Chicago, IL (US)

( * ) Notice: Subject to any disclaimer, the term of this patent is extended or adjusted under 35 U.S.C. 154(b) by 187 days.

(21) Appl. No.: 13/456,485

(22) Filed: Apr. 26, 2012

(65) Prior Publication Data

US 2013/0286467 A1   Oct. 31, 2013

(51) Int. Cl.
*H01S 3/30* (2006.01)
*G01J 3/44* (2006.01)

(52) U.S. Cl.
USPC ............................................ 359/344; 356/301

(58) Field of Classification Search
USPC ............ 359/334; 977/834, 953, 954; 356/301
See application file for complete search history.

(56) References Cited

U.S. PATENT DOCUMENTS

| | | | |
|---|---|---|---|
| 5,670,279 A * | 9/1997 | Goldstein | 430/5 |
| 6,819,692 B2 * | 11/2004 | Klimov et al. | 372/39 |
| 7,150,910 B2 * | 12/2006 | Eisler et al. | 428/325 |
| 7,450,227 B2 * | 11/2008 | Dwight et al. | 356/301 |
| 2003/0068496 A1 * | 4/2003 | Wei et al. | 428/402 |
| 2006/0054881 A1 * | 3/2006 | Li et al. | 257/19 |
| 2010/0053610 A1 * | 3/2010 | Lee | 356/328 |
| 2010/0256016 A1 * | 10/2010 | Blair et al. | 506/13 |
| 2010/0284001 A1 * | 11/2010 | Moskovits et al. | 356/301 |
| 2011/0267614 A1 * | 11/2011 | Reinhard et al. | 356/301 |
| 2012/0107958 A1 | 5/2012 | Poponin | |
| 2013/0242297 A1 * | 9/2013 | Thoniyot et al. | 356/244 |
| 2014/0104606 A1 * | 4/2014 | Shih | 356/301 |

OTHER PUBLICATIONS

Montgomery et al., "SERS Enhancements via Periodic Arrays of Gold Nanoparticles on Silver Film Structures", *Optics Express*, May 11, 2009, pp. 8669-8675, vol. 17, No. 10, OSA.

* cited by examiner

*Primary Examiner* — Eric Bolda
(74) *Attorney, Agent, or Firm* — Foley & Lardner LLP

(57) ABSTRACT

A method, system and article of manufacture for amplification of light for surface enhanced Raman spectroscopy. The method and system include a source of input light, a grating with grooves therein, a nanoparticle array disposed in the grooves with the nanoparticles and grating having a variety of selectable parameters. The combination of the nanoparticles and selected characteristics, including generating hot spots, and the features of the grating enable enhanced amplification of the input light signal to provide an output Raman signal of greatly increased intensity for Raman spectroscopy.

20 Claims, 16 Drawing Sheets

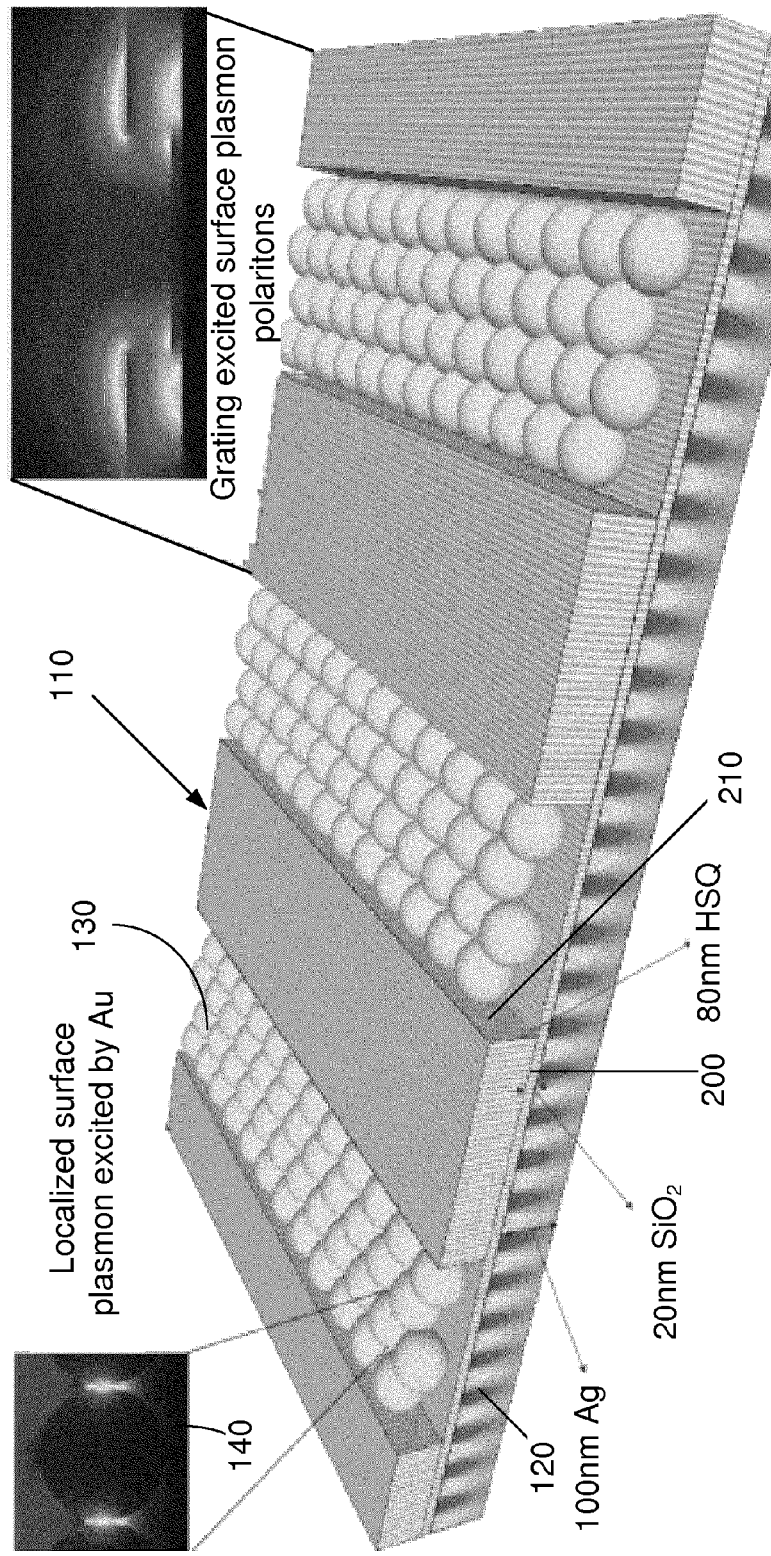
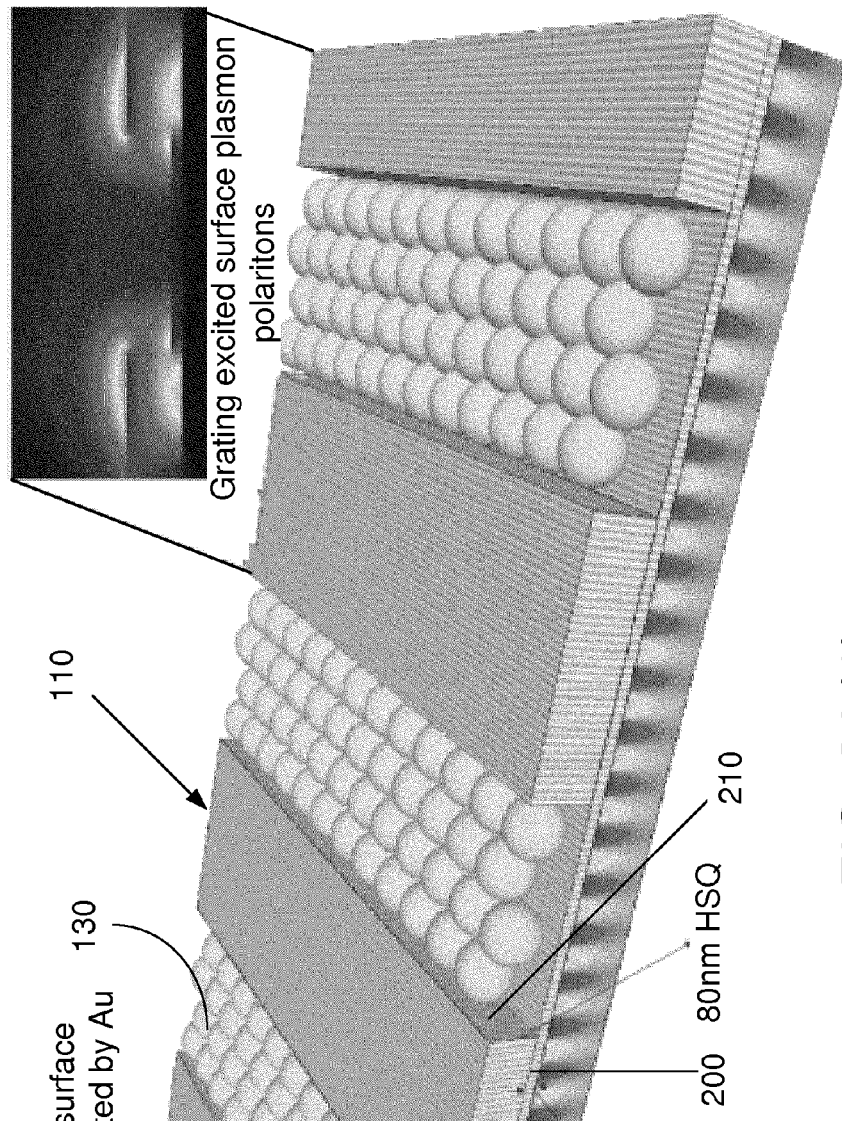
FIG. 2A(1)
FIG. 2A(2) Localized surface plasmon excited by Au
FIG. 2A(3) Grating excited surface plasmon polaritons FIG. 2B(1)
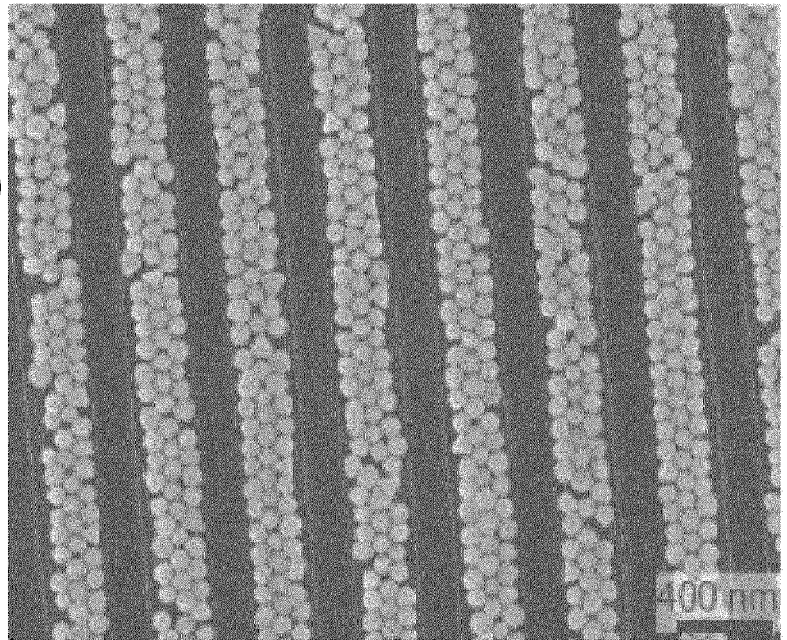
FIG. 2B(2)
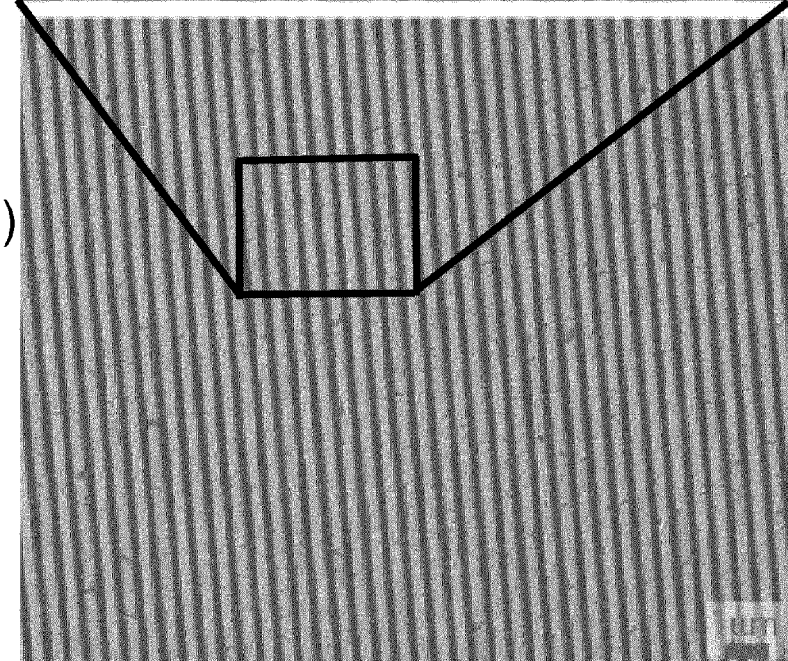

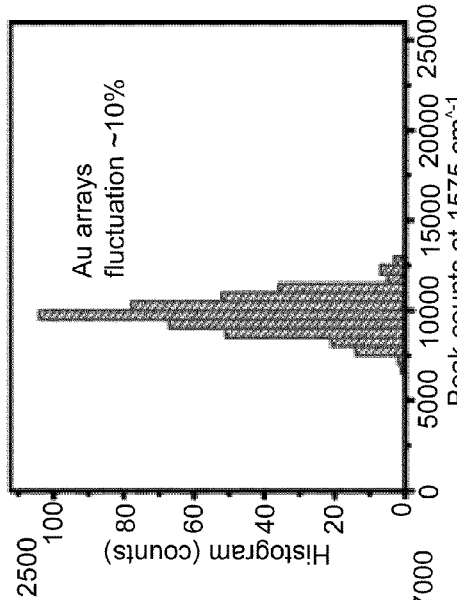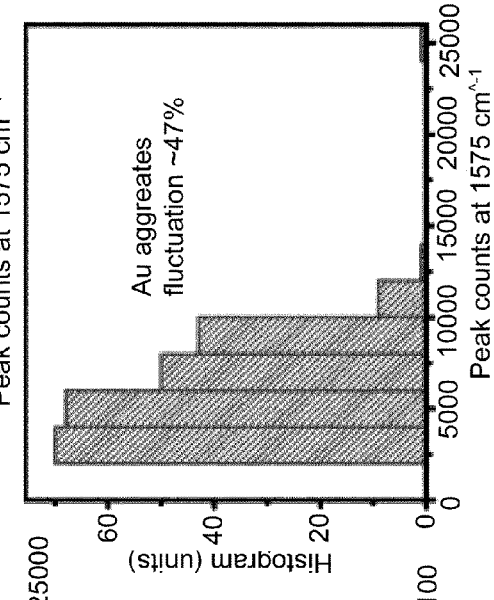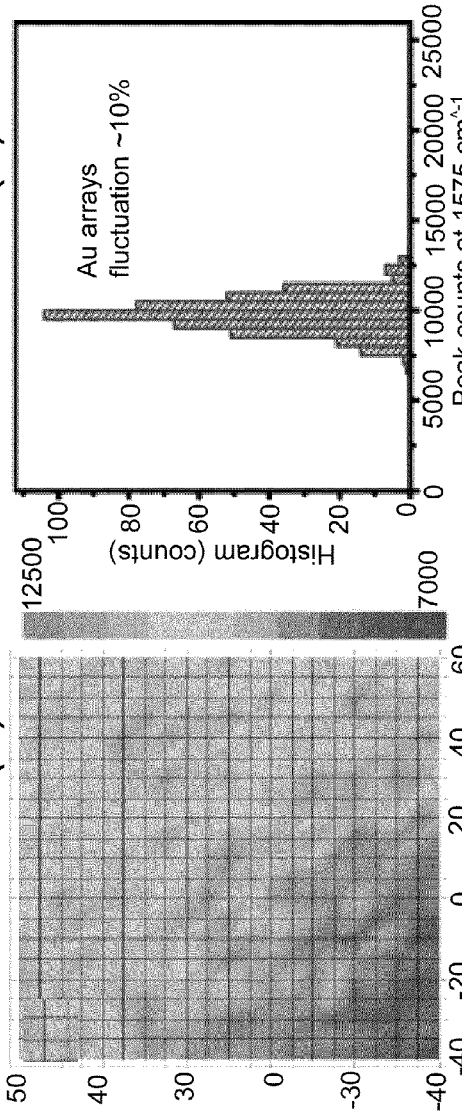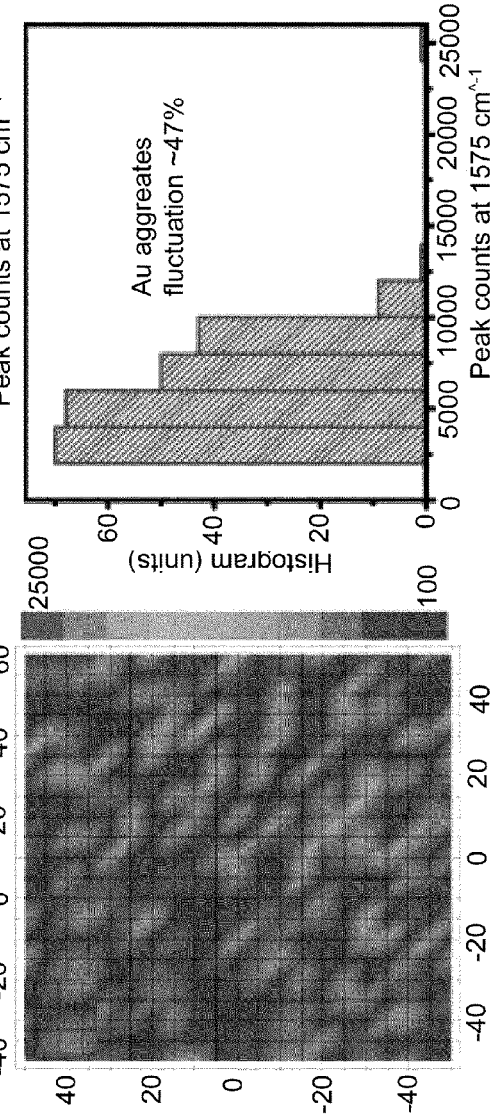

FIG. 4A     FIG. 4B
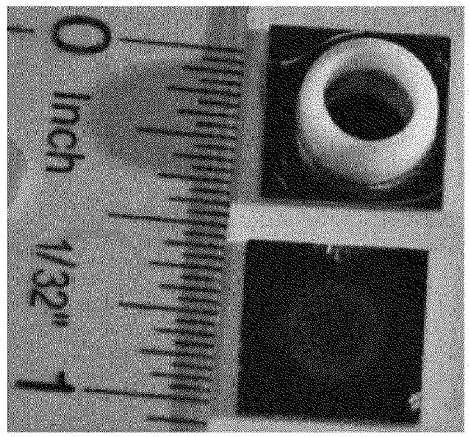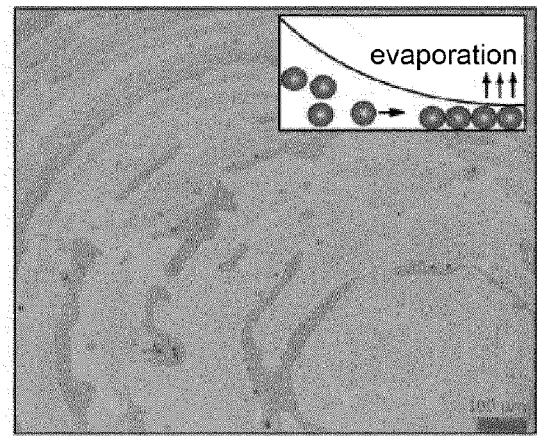
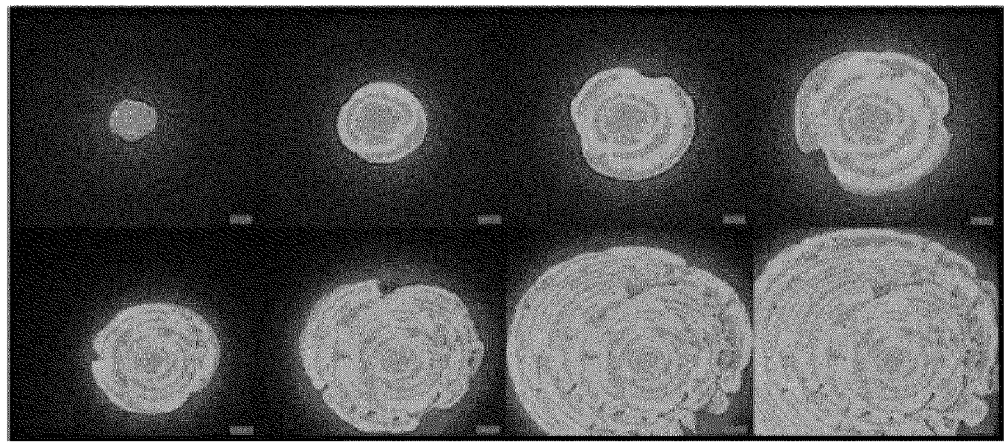
FIG. 4C

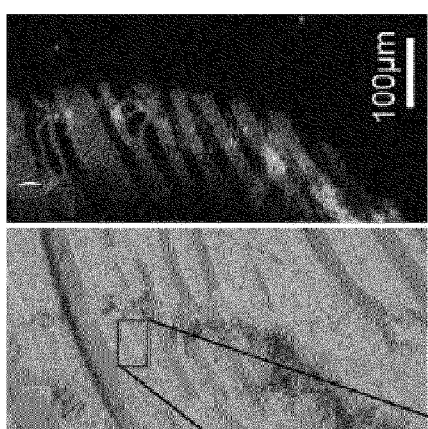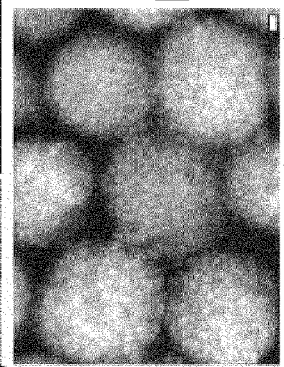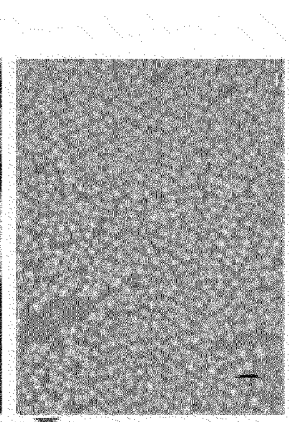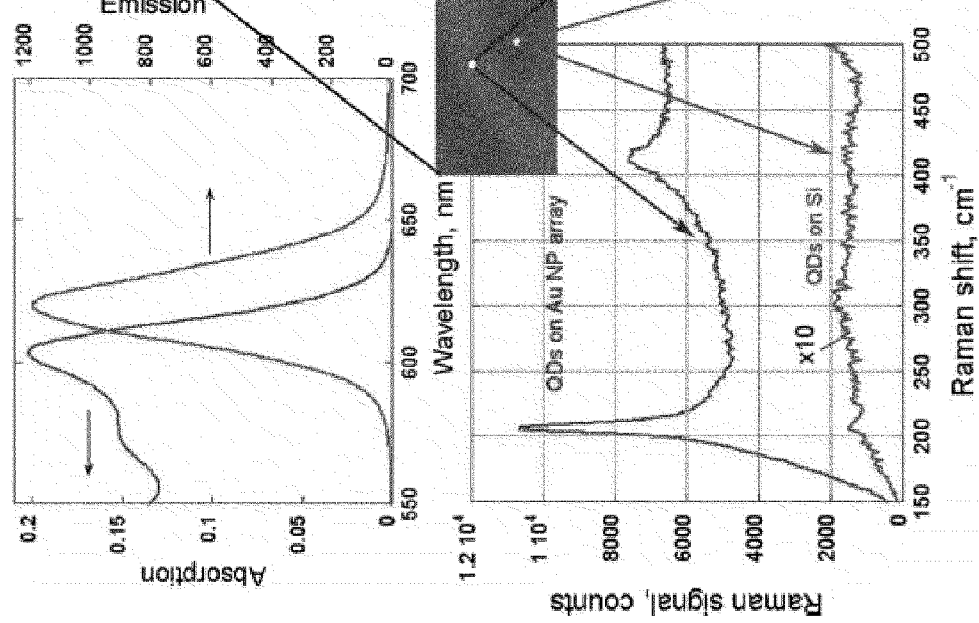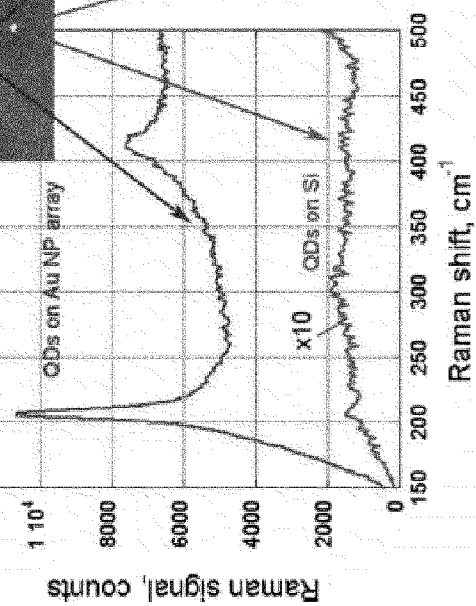
FIG. 8A  FIG. 8B  FIG. 8C  FIG. 8D  FIG. 8E  FIG. 8F

MULTISCALE LIGHT AMPLIFICATION STRUCTURES FOR SURFACE ENHANCED RAMAN SPECTROSCOPY

STATEMENT OF GOVERNMENT RIGHTS

The United States Government claims certain rights in this invention pursuant to Contract No. DE-AC02-06CH11357 between the United States Government and UChicago Argonne, LLC representing Argonne National Laboratory. The United States Government also claims certain rights in this invention pursuant to research sponsored by the Army Research Lab, ANL Cost Code 8R26900.

FIELD OF THE INVENTION

The inventor is directed to a system, method and article of manufacture for surface enhanced Raman spectroscopy. More particularly, the invention is directed to enhancing detectability of Raman scattered light by amplifying a signal arising from plasma resonances on surfaces and at aggregated nanoparticles in metal colloids. In addition, the invention is concerned with a system with particles arranged with particular interparticle gaps which assist in light amplification and using a high density of amplification hot spots for initial amplification. Further, the invention is directed to use of metal layer plasmons and a same resonant frequency for various amplification scales to provide additional amplification and also selecting a grating to create a resonance at particular frequencies.

BACKGROUND OF THE INVENTION

Raman spectra are a unique fingerprint of chemical molecules that are produced by exciting the vibrational modes of the various atoms forming the molecule by using monochromatic light. The strength of the Raman scattered light relative to the incident light, is very small and usually requires a large amount of chemical molecules and high light powers for the spectra acquisition. Optical spectroscopy, such as Raman spectroscopy, is very important for the detection and recognition of biological molecules including, for example, cancer genes, important proteins and DNA nucleotides. Among these optical techniques, Surface-Enhanced Raman Scattering ("SERS" hereinafter) has attracted considerable attention since it may allow the investigation of exceedingly small sample volumes and even single molecules. However, practical application of this new tool turns out to be very difficult due to the complicated interpretation and low fidelity of the acquired spectra.

The reason for such difficulties lies in the mechanism of SERS: SERS is based on the huge amplification, by up to about $10^4$, of the local optical fields at nanoscale roughness of metal substrates or metal nanoparticles ("hot spots") that are induced by plasmon resonances. Molecules residing in these enhanced fields are so strongly excited that they can be detected in a Raman spectrum. Developing SERS based detectors and analyzers, however, faces a major challenge in the difficulty of finding SERS-active substrates that display these enhancements in both reliable and efficient ways. Currently there are several known commercial options available for unspecified and label-free SERS analysis. One option is from D3 Technologies (www.d3technologies.co.uk) and Mesophotonics (http://www.mesophotonics.com/sers_central/what_is_klarite.html), now part of Renishaw (http://www.renishawdiagnostics.com/en/klarite-sers-detection-substrates—12515). These technologies concern gold coated textured silicon based photonic crystal substrates that are fairly reliable but are not sensitive enough for single molecule detection. Another type of approach for SERS is from Real Time Analyzers Inc (www.rta.biz) offering vials of silver particles in a sol-gel solution. These latter "substrates" provide high sensitivity. However, there are only a few hot-spots randomly distributed in the vials and most of the solution is not SERS-active which yields spectra of low fidelity.

SUMMARY OF THE INVENTION

This method, system and article of manufacture is directed to design, implementation and use of precisely controlled SERS-substrates enabling a multistage amplification of the light fields for high fidelity SERS spectroscopy. One stage of amplification arises from controlled hot-spots in the regular interparticle gap lattice of self-assembled arrays of monodisperse spherical metal/dielectric core/shell nanoparticles. Another feature is designed to increase the SERS enhancement further, and concerns the use of components for producing additional stages of optical amplification. Another aspect of light enhancement for SERS is the electromagnetic coupling of particles to surface plasmon polarilons ("SPP" hereinafter) on a metal film substrate. Yet a further aspect involves use of particular types of grating templates for the assembly of nanoparticles; and the grating is disposed on a metal mirror and the grating filled with the nanaoparticles with each component adding to the enhancement. In an additional aspect, a same resonant frequency is used to provide various scales of amplification. Yet another aspect is forming a high density of the controlled hot spots for initial amplification and then followed by use of other features to produce an amplified result.

By introducing periodic modulation of the metal film, intense standing waves are formed through Bragg reflection leading to an additional increase in the surface field and SERS enhancement. The grating effect due to the periodic structure also enables efficient directional emission of the Raman light at the Bragg angle. The implementation of our preferred design is based in part on the self-assembly of gold (and other useful elements) periodic densely packed nanoparticle arrays in the lithographically patterned grating templates on a silver film covered with a silicon dioxide spacer. Our approach is straightforward, easy to scale up to large areas, and yields substrates with substantial and reproducible SERS gains enabling greatly improved SERS methods for numerous commercial applications.

These and other advantages and features of the invention, together with the organization and manner of operation thereof, will become apparent from the detailed description when taken in conjunction with the accompanying drawings.

BRIEF DESCRIPTION OF THE DRAWINGS

FIG. 2A(1) is a schematic of a SERS substrate; FIG. 2A(2) is an insert enlargement showing localized surface plasmons excited in a Au array; and FIG. 2A(3) shows an insert enlargement of a grating excited surface plasmon polaritrons; FIGS. 2B(1) and 2B(2) show various top view enlargements of a portion of the SERS substrate of FIG. 2A(1)

FIG. 3A(1) shows 2D scans of a Raman signal on a self-assembled 80 nm Au nanoparticles; with FIG. 3A(2) the accompanying plot of a histogram of the signal; and FIG. 3B(1) is a 2D scan of the Raman signal on an irregular colloidal substrate; and FIG. 3B(2) is an accompanying histogram for FIG. 3B(1); comparison of the Raman scans and histograms shows large areal reproducibility and high average enhancement factor for the regular nanoparticle array;

FIG. 4A shows a Teflon-ferrule glued on a ½ inch Si substrate; FIG. 4B shows optical image of the 80 nm Au nanoparticle arrays (monolayers of nanoparticles: light gray, double layers: dark gray, and bare Si: gray); the inset shows a scheme of the nanoparticle assembly during solvent evaporation; FIG. 4C shows a sequence of frames illustrating the self-assembly of 80 nm Au nanoparticles from the water solution, wherein the meniscus of the liquid colloid moves from the center of the ferrule to the periphery, and intervals between the frames are 500 s in the top row and 5000 s in the bottom row. (Scale bar: 200 µm.);

FIG. 8A shows absorption and emission spectra of 5 nm CdSe QDs; FIG. 8B shows Optical image of the sample surface with a dried ring of QDs covering bands of the Au nanoparticle monolayers (light gray or "g"), double layers (dark gray or "dg"), and bare Si (gray or "b"); dark deposits are dried ligands from the solvent; FIG. 8C shows PL image of the area shown in FIG. 8B; FIG. 8D shows SERS spectra of the QDs on the Au nanoparticle monolayer (top curve) and on bare Si (bottom curve, the signal is multiplied by 10); the inset shows a 2D SERS scan at the 207 cm-1 peak wavelength and the scan area is outlined by the box in FIG. 8B; arrows point to the SERS spectra acquisition spots; FIGS. 8E and F show SEM images in these spots reveal the same density of QDs on Au nanoparticles (FIG. 8E) and on bare Si (FIG. 8F). (Scale bars in (e) and (f): 10 nm).

DETAILED DESCRIPTION OF PREFERRED EMBODIMENTS

Figure 1C:
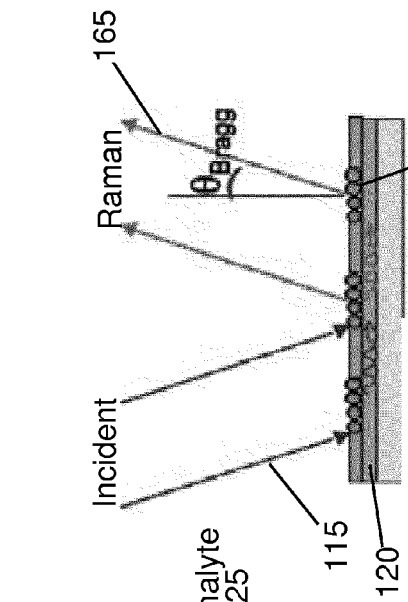
FIG. 1C shows grating coupling of incident light and outcoupling of a Raman signal.
Figure 1B:
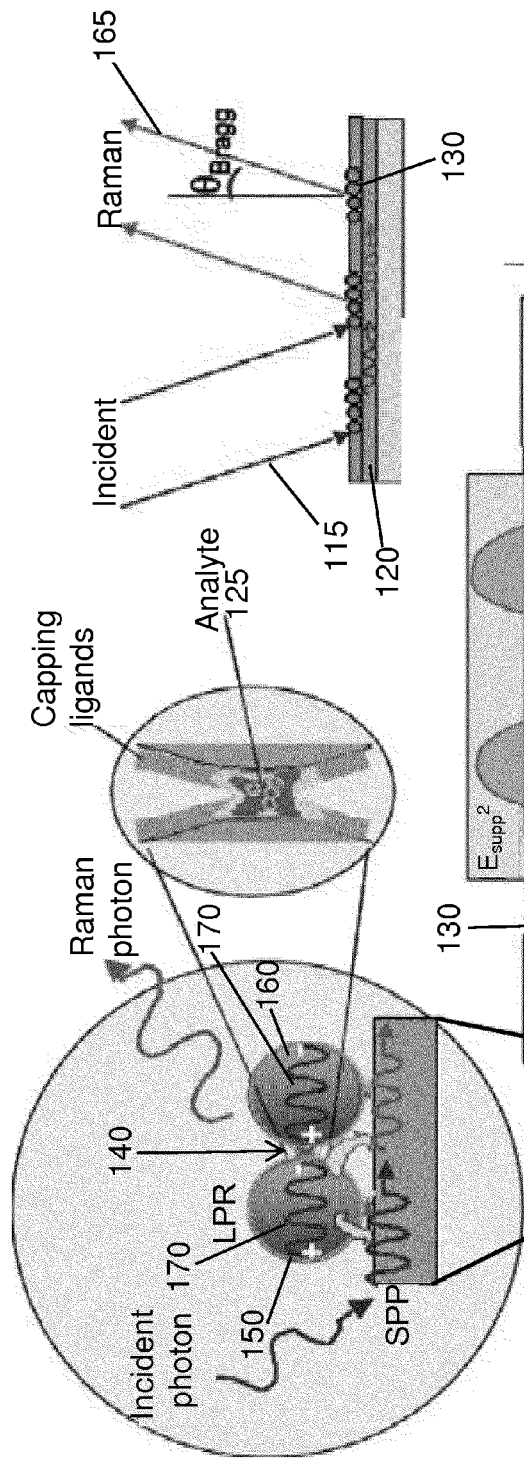
FIG. 1B shows an insert from FIG. 1A and illustrates schematically the transformation of light into propagating surface plasmons on the grating and local plasmon frequencies of interacting nanoparticles with an analyte disposed between the particles.
Figure 1A:
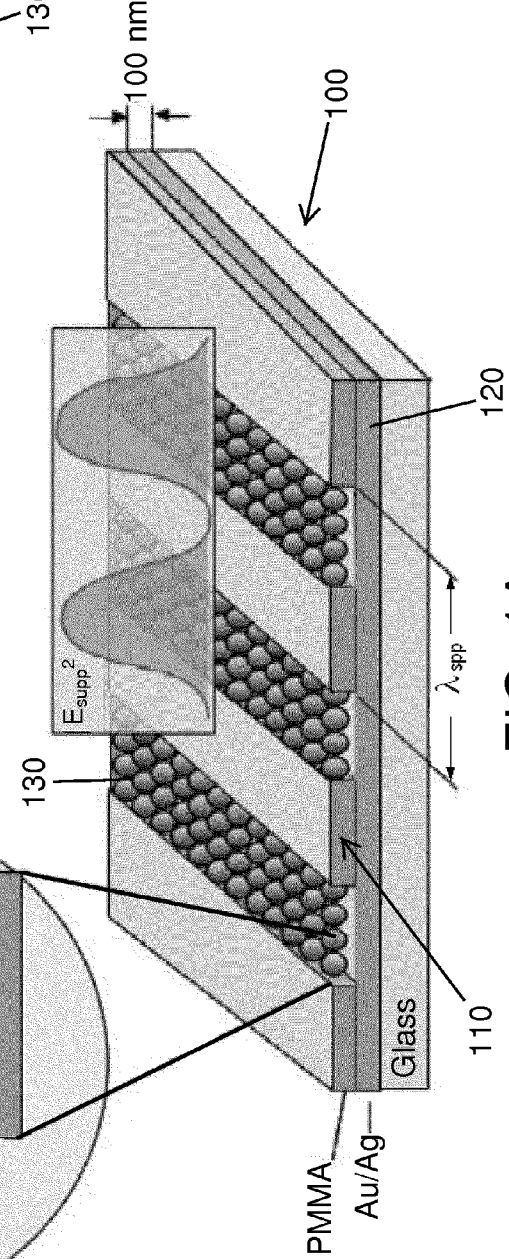
FIG. 1A shows a preferred form of a SERS substrate.

In a preferred embodiment, surface enhanced Raman spectroscopy ("SERS" as mentioned hereinbefore) and associated articles of manufacture, methods, and system), are provided. SERS embodiments described herein arise from combining a number of synergistic mechanisms of light signal enhancement to generate a greatly amplified signal characteristic of a local light intensity. In these embodiments, strong light enhancement from different resonance structures are coupled via a multiscale periodic SERS array 100 shown in FIG. 1A, wherein resonances of the constituents are tuned to a same frequency to enable multiple amplification of the light signal output for Raman spectroscopy. The highest amplification can be achieved by virtue of a mathematical product of enhancement factor from separate elements of the SERS array 100. In addition, strong interactions between the separate components of the SERS array 100 can expand the spectral range of light amplification. As shown in FIGS. 1A-1C, the array 100 includes one or two dimensional metal gratings 110 which form a distributed cavity with a resonance frequency that can be tuned to eigen modes of other components of the SERS array 100 by varying period of its grating 110. The gratings also have a period equal to a wavelength of surface plasmons having a frequency associated with incident light 115. This grating 110 performs the transformation of three-dimensional incident waves of the light 115 into a two-dimensional surface mode and thus condenses the light energy into a narrow surface layer yielding a first stage of amplification. At the same time, the periodic grating 110 acts as a distributed resonator and provides a second stage of electromagnetic amplification through the excitation of intense standing surface waves. The pitch of the grating 110 consists of two sections, one a dielectric covered metal surface 120 and the other a self-assembled array of metal nanoparticles 130. The combination of the dielectric grating 110 on the metal surface 120 acting like a mirror alone provides enhancement of the light 115 after interaction with these components. The array of nanoparticles 130 has plasmon resonances combined of multipolar modes of individual ones of the nanoparticles 130. At these resonances the light field has a very large enhancement in the nanoscale interparticle gaps ("hot spots" hereinafter) 140 (for example, see FIGS. 1B, 2A(2) and 7). The most preferred embodiment combines all features, such as, the dielectric coated grating 110, the metal surface 120 and the nanoparticles 130 all resonating at the same frequency which provides the complementary product of each contributing feature to provide greatly increased enhancement of output light signal 160.

The solid metal nanoparticles 130 with different coating 150 (to effect adjustment of resonance behavior) and metal nanoshells 165 (to effect adjustment of resonance behavior) with dielectric cores 170 can be used. Interactions of the particles 130 with the metal surface 120 introduces an additional amplification of the light intensity output for the case of dielectric gratings 110. Additional "hot spots" 140 can be introduced near the metal surface 120/nanoparticle 140 contact. Also, these interactions red-shift and expand resonances of the particle array 140. Adding a dielectric spacer 145 between the metal surface 120 and the nanoparticles 130 allows the regulation of the array 130/metal surface 120 coupling strength and thus enhancement of intensity and resonance frequencies.

By changing the period of the gratings 110, its resonance is tuned to the plasmon resonance of the array of the metal nanoparticles 130, which in turn can be tuned by varying the size, material, shape (e.g., (1) all one size but different selectable size and (2) of mixed size) and interparticle gap of the nanoparticles 130, the spacing of the nanoparticles 130, nature of the interparticle gap (physical and chemical) density of the hot spots 140 between the nanoparticles and also between the nanoparticles 130 and the metal substrate (the surface 120). These variations in structural features provide another type or stage of amplification. Because of the multiple amplification stages, or different categories of amplification and combinations thereof, the structure of the SERS array 100 offers much larger enhancement factors than prior art SERS systems. Another advantage is the direct transformation of the light 115 into surface modes on the metal surface 120 and more efficient coupling to the nanoparticle resonances due to the grating effect without dedicated optics and prism coupling implemented in current commercial SERS devices. The out-coupling of a Raman signal into scattered light 160 is provided by the same grating 110 and offers a high directionality due to diffraction and thus easier detection. Another advantage is a homogeneous distribution and high density of the hot spots 140 between the nanoparticles 130 and large area for binding analyte molecules 125 to the nanoparticles 130 that offers increased fidelity of the SERS signal. Also, particle surfaces 170 can be specifically functionalized for the chosen analyte 125 and work as a sensor for detecting any particular one of the analyte 125.

In a preferred form of the invention, tuning of the SERS array 100 resonances is performed by introduction of additional phases. First, a continuous nanoparticle array 130 is assembled on the metal substrate 120 covered with the thin dielectric spacer 200/210 and spectral parameters of the array 100 are measured. Then the grating 110 period is chosen and manufactured on the metal substrate 120 with the dielectric spacer 145 to support the array resonance frequency. Finally, the nanoparticle arrays 130 are assembled in the groves of the gratings 110 on the metal substrate 120. In this final structure grating resonances coincide with resonances of the nanoparticle array 130 in the groves and yield maximum light enhancement in the interparticle hot spot gaps 140.

FIG. 1A further shows details of the design of the proposed SERS substrate array 100. A photoresist produced layer (PMMA or HSQ 210, see FIG. 2A(1)) is only one of possible implementations of the grating 110 on the metal film surface 120, preferably of Au or Ag. The left insert FIG. 1B shows schematically the transformation of the incident light 115 into the propagating surface plasmons on the grating 110 and into local plasmon resonances of the nanoparticles 130 interacting with each other. The standing surface plasmon wave formed due to the grating resonance has maximum intensity around the nanoparticle array 130 and provides better coupling to the latter. The right insert FIG. 1C shows the principle of grating coupling of the incident light 115 and outcoupling of the Raman signal in the scattered light 165, which contains information about the analytic molecules 125 located between the nanoparticles 130.

In one preferred implementation of the SERS substrate or array 100 several steps can be used: 1—sputtering of 100 nm silver film 200 on Si or $SiO_2$ substrate with 20 nm Cr adhesive layer. 2—deposition of a thin $SiO_2$ film 205 per FIG. 2A(1) (20-40 nm), 3—e-beam or optical lithographical patterning of the gratings 110 using 100 nm thick HSQ 210 or optical resist, 4—capillary self-assembly of densely packed arrays of 80 nm gold nanoparticles in the gratings 110 between the HSQ ridges using controlled cover slip motion over the colloidal solution of the nanoparticles 130.

Figure 2C:
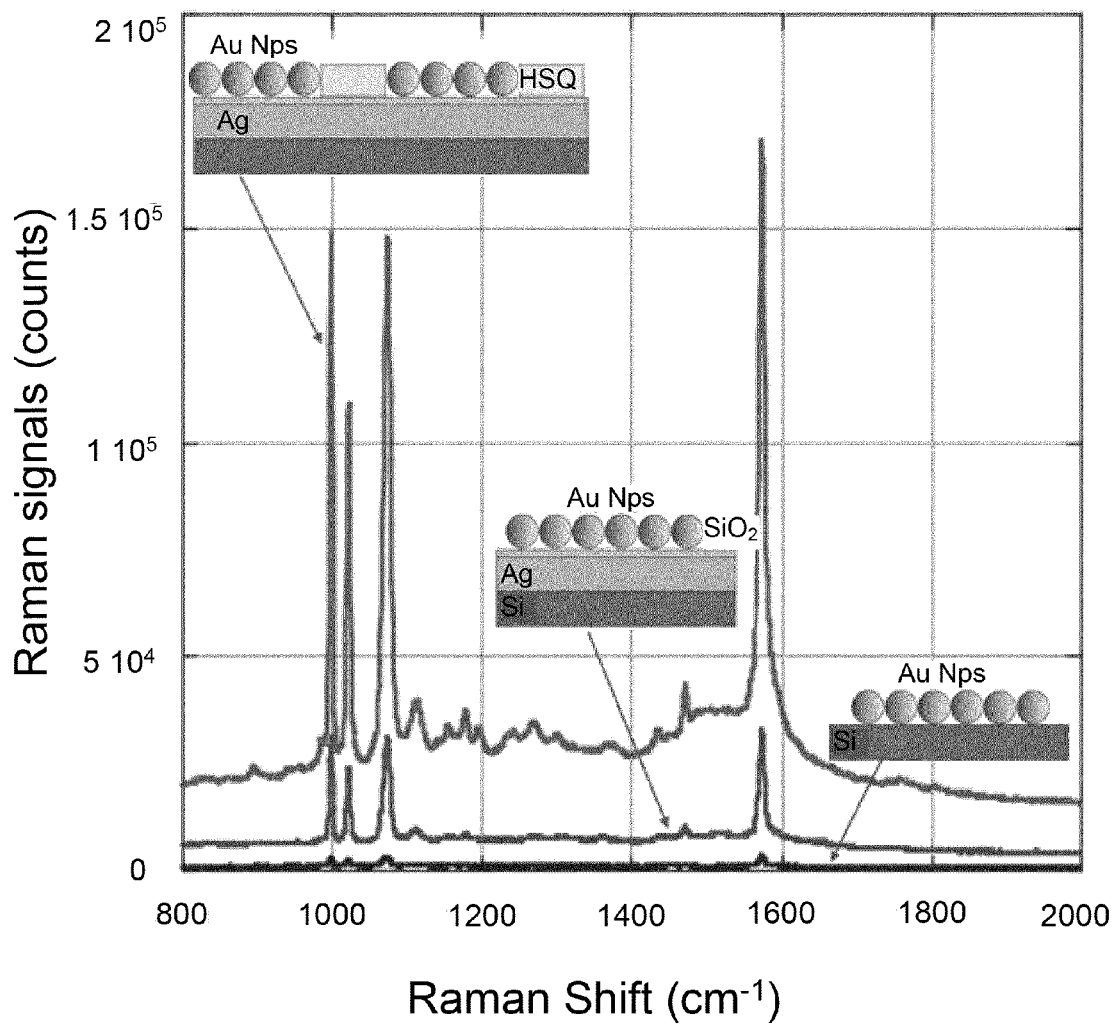
FIG. 2C shows a comparison of SERS signals from Benzenthiol molecules for the cases on Au particle arrays on a Ag film with a 20 nm SiO$_2$ spacer (top curve) on gratings, Au particle arrays on a Ag film with 20 nm SiO$_2$ spacer (middle curve), and Au particle arrays on a Si substrate (bottom curve)

Prototypes of the SERS substrates 100 confirmed giant, or very large, amplification of light and high fidelity and homogeneity of the SERS signals from Rhodamine 6G and Benzenethiol molecules (see, for example, FIGS. 2A-2C). FIG. 2C illustrates two example consecutive steps of the light amplification upon inclusion of additional resonant elements into the overall structure, which is revealed by appropriate enhancement of the SERS signal from benzenethiol molecules. The areal map of the Raman signal confirms much better homogeneity; and thus much better fidelity of the SERS acquisition is attained by using the nanoparticle array 130 compared to an irregular colloidal substrate 135 is shown in FIGS. 3A(1)-3B(2). Similar SERS type substrates 100 can also be used for improving efficiency of solid state lighting devices and light harvesting applications which is apparent to one of skill in the art applying the embodiments described herein.

In another aspect of the invention, the above described "hot spot" structure 140 can be created effectively to enhance light amplification for SERS via the substrate array 100. A simple and cost-effective large-scale self-assembly of large (80 nm) colloidal Au nanoparticle arrays 130 can be prepared with regular ≈1 nm gaps and extended up to a few hundred micrometers, which is noticeably larger than monocrystalline areas known in the art for large metal nanoparticles. Optical spectra from such arrays 100 are modified by the strong coupling between the Au nanoparticles 130, as confirmed by finite-difference time-domain (FDTD) calculations. A strong light amplification is found in our structures by measuring SERS and photoluminescence (PL) signals of 5 nm CdSe quantum dots ("QD"s hereinafter) and directly evaluate the enhancement factors by imaging and counting QD reporters using high-resolution scanning electron microscopy (SEM). This procedure yields an electromagnetic SERS enhancement of about $10^4$ at 514 nm excitation wavelength for relatively large QDs occupying regions outside the narrowest gap (or the hotspot 140). In spite of that, the design, which benefits from the extension of the high-intensity regions between large nanoparticles 130 and the large density of the periodic hot spots 140, provides strong and stable Raman signals from few-micrometer areas. The advantages of the high uniform density of the hot spots 140, their easy access for analytes, and a cost-effective self-assembly process for their manufacture show the potential of properly designed large nanoparticle arrays 130 for SERS applications. Their ability to generate a much larger enhancement factor of $\approx 10^8$ is confirmed at larger excitation wavelengths for benzenethiol (BT) molecules filling the interparticle gaps 140. Even larger enhancement factor of ~$10^{10}$ is obtained for the substrate SERS arrays 100.

The following non-limiting Examples provide illustration of various aspects of preparing materials for contraction and use of the SERS substrate 100.

Example I

The following provides experimental details concerning preparation of the SERS substrates 100. Large ordered Au nanoparticle arrays 130 on planar silicon substrates 180 or indium tin oxide (ITO)-covered glass slides 190 (see FIG. 1A) were fabricated by solvent evaporation in a Teflon ferrule. This approach was successfully used for the assembly of large colloidal crystals of polystyrene particles with 47 nm to 2 μm diameters. To implement this technique for the assembly of large Au nanoparticles, key parameters were adjusted to control the process, such as nanoparticle concentration, surface tension and purity of the solvent, the evaporation rate, and number of capping ligands on the nanoparticle surface. We used 80 nm Au nanoparticles and tuned the thickness of the capping ligand layer by several cycles of centrifugation followed by the replacement of the solvent with deionized water (18.2 MΩ cm). The purified and concentrated colloidal solution of Au nanoparticles was then injected into a Teflon ferrule glued with rubber cement on Si or ITO covered glass substrates, as shown in FIG. 4A. The ferrule was covered with a glass slip to reduce the evaporation rate and the self-assembly process was monitored using an optical microscope and computer-controlled digital camera. In the course of drying, the colloidal droplet acquired a concave shape with a minimum thickness in the center of the ferrule. When the depth of the thinning water layer became equal to the particle diameter, capillary interactions forced the Au nanoparticles to start assembling at the liquid/substrate contact line. This process is similar to the colloidal assembly of polystyrene spheres. Convective flow induced by solvent evaporation at the drying front dragged nanoparticles from the bulk of the solution towards the contact line, thereby assisting the crystal growth there (see inset in FIG. 4B). Depending on the particle concentration, a monolayer or multiple layers were deposited. Usually, the number of layers increased abruptly from one to two during the crystal assembly. As shown in FIG. 4C, monolayer and double-layer bands formed quasiperiodically along the direction of the meniscus motion, alternating with empty bands. Such a banding process is often observed in capillary self-assembly experiments and is associated with the stick-slip motion of the contact line. FIG. 4C presents a typical sequence of pictures appearing during the drying process. Images were taken in 10 s intervals using an Olympus X61 microscope with a long-distance 5x objective. The nanoparticle concentration had a strong effect on the band spacing and could essentially change the geometry of the pattern (See FIGS. 9A-9D).

Figures 5A, 5B, 5C, 5D:
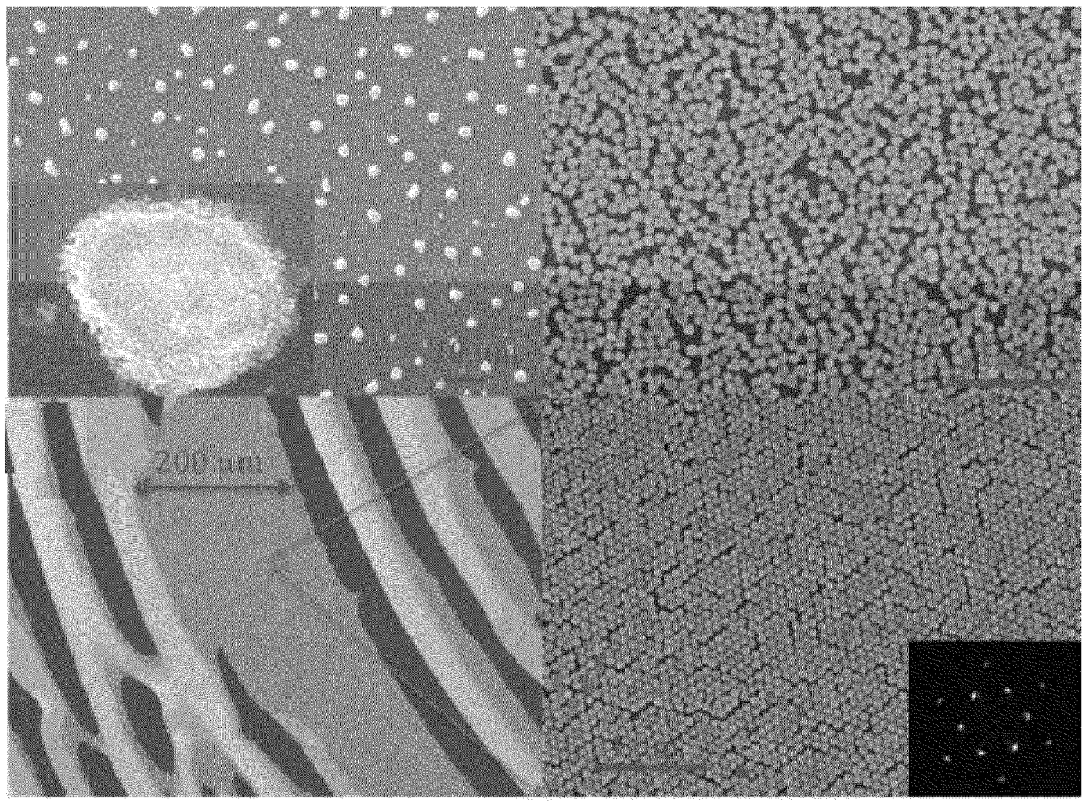
FIG. 5A shows an SEM image of a 80 nm Au nanoparticle array assembled by aggregation of nanoparticles after the excess clean-up of ligands (the inset shows a close-up view)
FIG. 5B shows disordered monolayer of nanoparticles formed after insufficient clean-up of ligands.
FIG. 5C (high magnification) and FIG. 5D (low magnification) show hexagonal closepacked (hcp) nanoparticle arrays obtained after tuning the clean-up procedure; the FFT pattern in the inset confirms good ordering of the nanoparticles.

The assembly process is very sensitive to this cleaning procedure. After an excess removal of the ligands, the nanoparticles aggregate as shown in FIG. 5A. However, insufficient cleaning leads to a strong repulsion of the nanoparticles and their dispersion on the substrate, as illustrated in FIG. 5B. After a few cycles of centrifugation (see Experimental Section) and final dilution to a concentration of ≈$1.0 \times 10^{11}$ mL$^{-1}$ and 30-50 μL initial solution volume, we obtained few-millimeter-long and, on average, more than 100-μm-wide bands. The SEM image in FIG. 5C shows a high degree of ordering in the bands, which is surprising given the large nanoparticle diameter scatter in the colloid used (7% monodispersity). Based on the recorded movie, we find a stable self-assembly speed of ≈0.1 μm s$^{-1}$ for a monolayer and 0.03 μm s$^{-1}$ for a double layer. The glass cover on the ferrule, which controlled the slow evaporation rate, assisted the formation of uniform crystalline structures and allowed us to obtain extended Au nanoparticle crystals over 200×1000 μm$^2$ areas, as shown in FIG. 5C. The close-up in FIG. 5D and fast Fourier transform (FFT) image in the inset confirm the good ordering of the structure. The whole area appears to be a single domain, although it contains linear "cracks" of slightly increased gaps between the particles. This is a typical feature of the evaporative assembly technique.

Figure 6A:
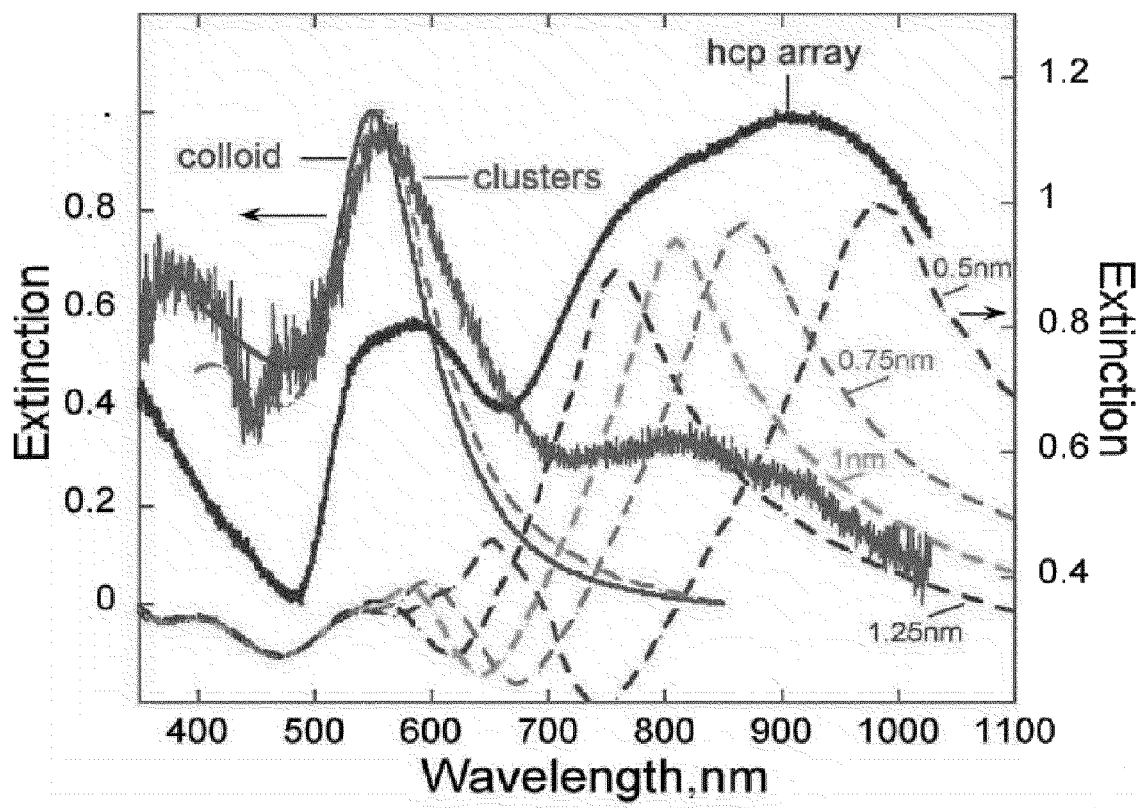
FIG. 6A shows extinction spectra (normalized by maximum value) of the aqueous colloid of 80 nm Au nanoparticles, Au nanoparticle hcp arrays on ITO-coated glass, and Au nanoparticle aggregates on ITO-coated glass; the dashed lines show FDTD calculated spectra of the colloid and ordered nanoparticle array with 0.5-1.25 nm gaps.

FIG. 6A shows the extinction spectra of an 80 nm Au nanoparticle colloid in a cuvette and of disordered and ordered Au nanoparticles deposited on transparent ITO-covered glass substrates. The extinction is defined as the negative logarithm of light intensity transmitted through the nanoparticle arrays normalized by the intensity transmitted through the pure substrate. While the aqueous Au nanoparticle colloid exhibits a single resonance near 550 nm, consistent with a dipolar Mie scattering on individual Au nanoparticles, ordered Au nanoparticle monolayers show a double resonance structure associated with a strong coupling between nanoparticles. Large individual Au nanoparticles can also show spectra with double maxima, where one of the resonances represents the red-shifted dipolar mode and the other corresponds to a developing blue-shifted quadrupolar mode. However, in the nanoparticle arrays the situation is more intricate. Here the resonances are formed by a series of interacting multipolar modes of the particles and coupling to the substrate. The results of FDTD calculations in FIGS. 6A-6C, which incorporate the geometrical details of our nanoparticle arrays and the 20 nm ITO/glass substrate, are in good agreement with the experimental spectra and show complex light-field patterns in the nanoparticle array at the "blue" (around ≈550 nm) and the "red" (around ≈850 nm) resonances. The double hump structure of the measured "red" spectral maximum in FIG. 6A can be well reproduced by assuming variations of the interparticle gap between ≈0.6 and ≈1 nm (see broken lines in FIG. 6A), in agreement with our transmission electron microscopy (TEM) estimates of the interparticle gaps (see FIG. 7). At the same time, the "blue" resonance is intrinsically constructed of two overlapping modes with different field patterns. Their splitting increases with decreasing interparticle gap. For a 1 nm gap these modes are at ≈520 and ≈585 nm. In contrast, the disordered Au aggregates show a broadened single-particle dipolar mode and strongly suppressed peak around ≈850 nm, which indicates a lack of long-range coupling.

Example II

Figures 6B, 6C:
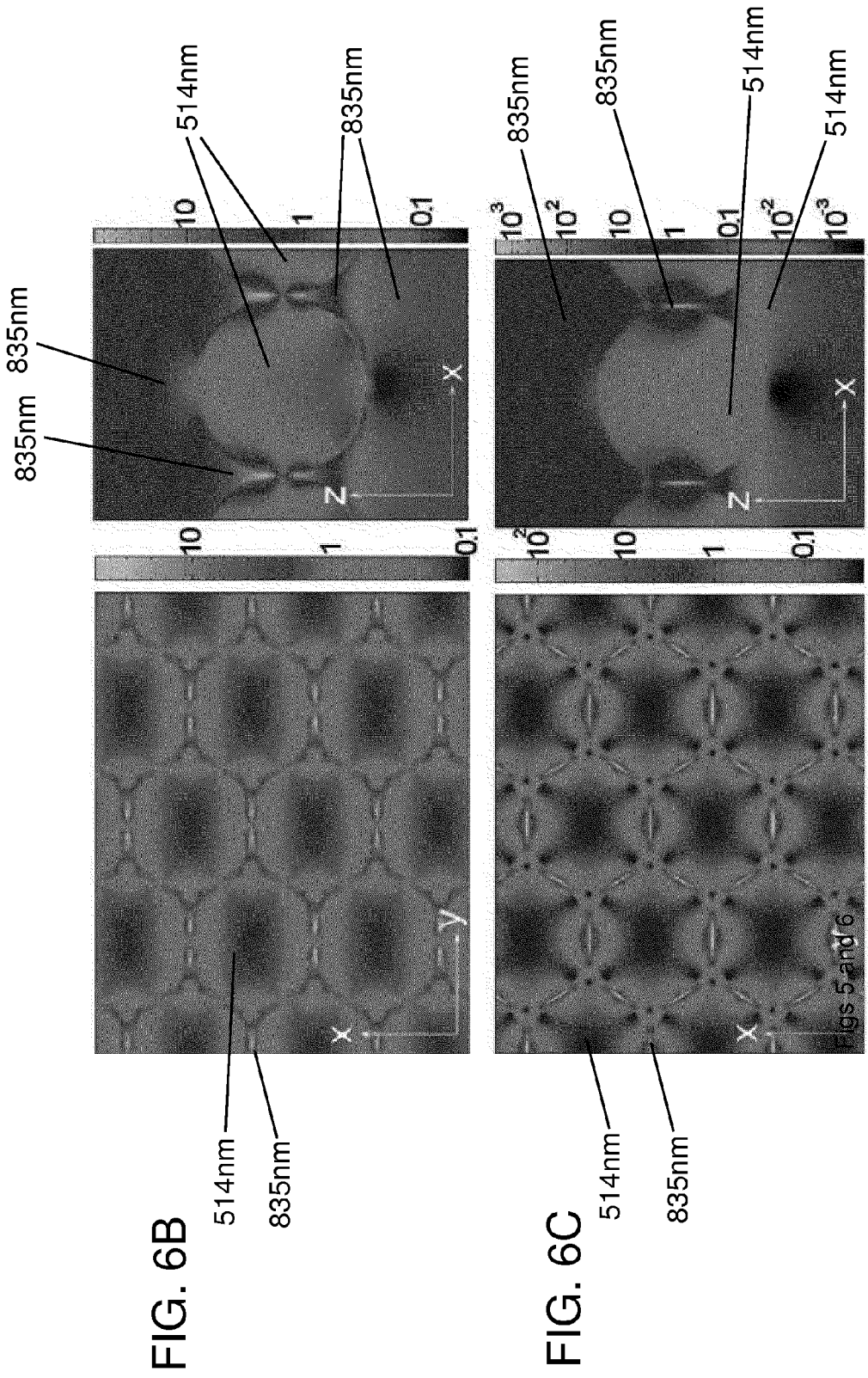
FIGS. 6B and 6C, respectively, show simulated light enhancement ($E^2/E 0^2$-incident) in the x-y and x-z planes crossing the centers of NPs, at 514 nm ("blue" resonance region) and 835 nm ("red" resonance) at 1 nm gap. z is the incidence direction of x-polarized light.
Figure 7:
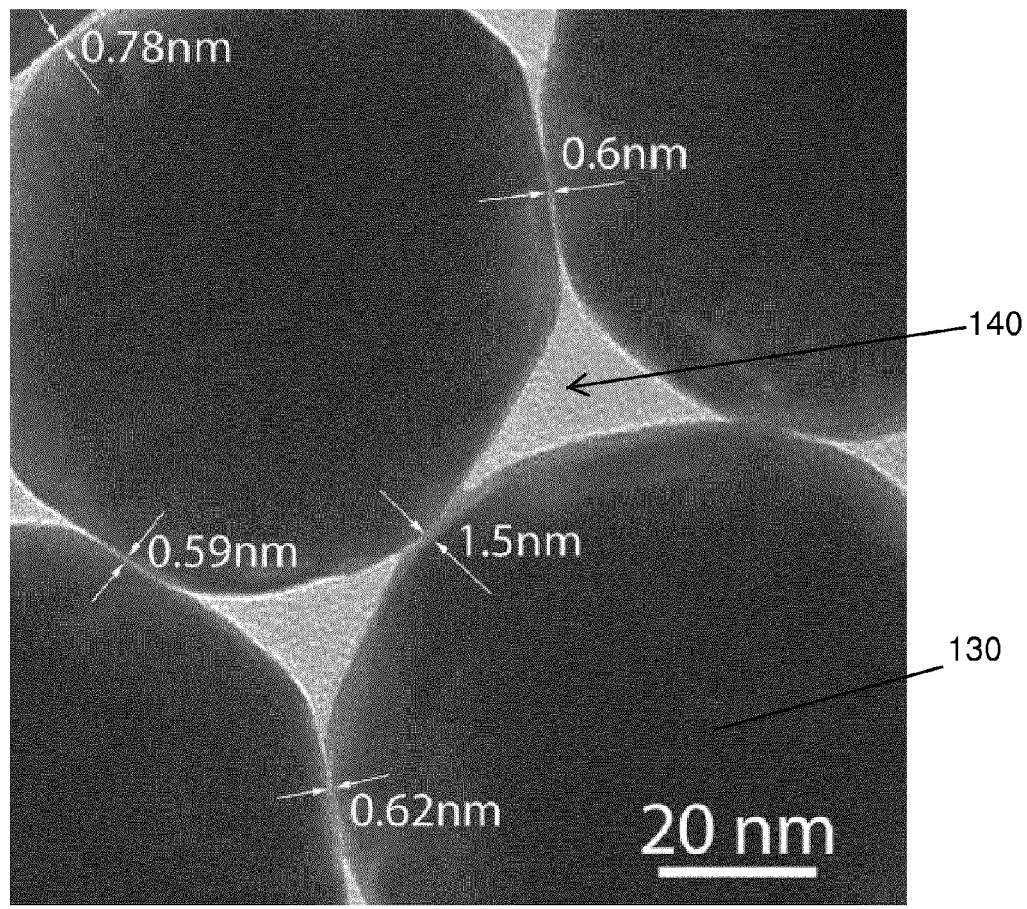
FIG. 7 shows high resolution TEM image showing the distribution of interparticle gaps between 80 nm Au arrays.
Figure 9A:
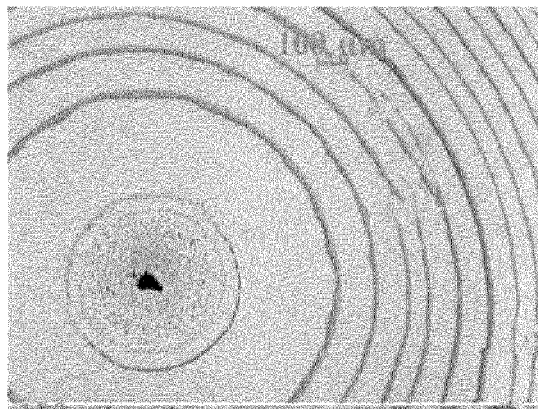
FIG. 9A shows optical images of a typical pattern generated by the capillary self-assembly in the Teflon ferrule on a Si substrate at different colloid concentrations; where gray corresponds to the bare silicon, (but including very dark gray feature "g") light gray to ordered monolayer, and dark gray-double-layer of Au nanoparticles; particle concentration in FIGS. 9A-9D varies from $1.3*10^{10}$, to $1.8*10^{10}$, $8*10^{10}$, $13*10^{10}$/ml and the pattern in FIG. 9B bears a striking similarity to a Sierpinski gasket.
Figure 9B:
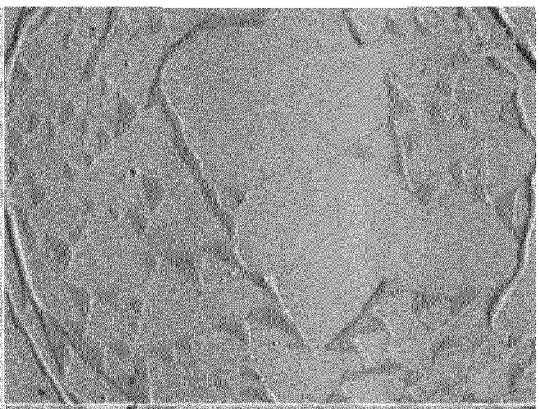
Figure 9C:
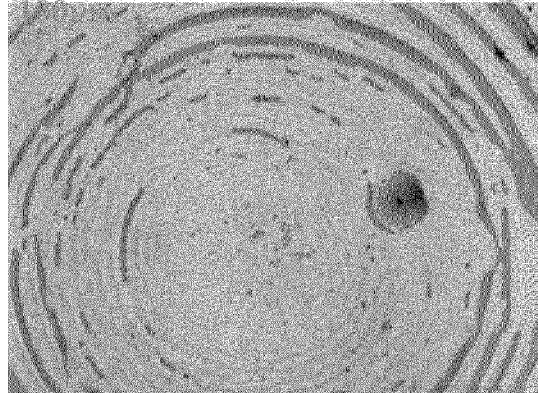
Figure 9D:
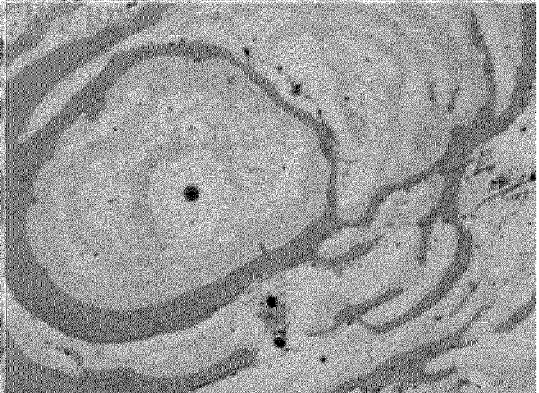
Figure 10:
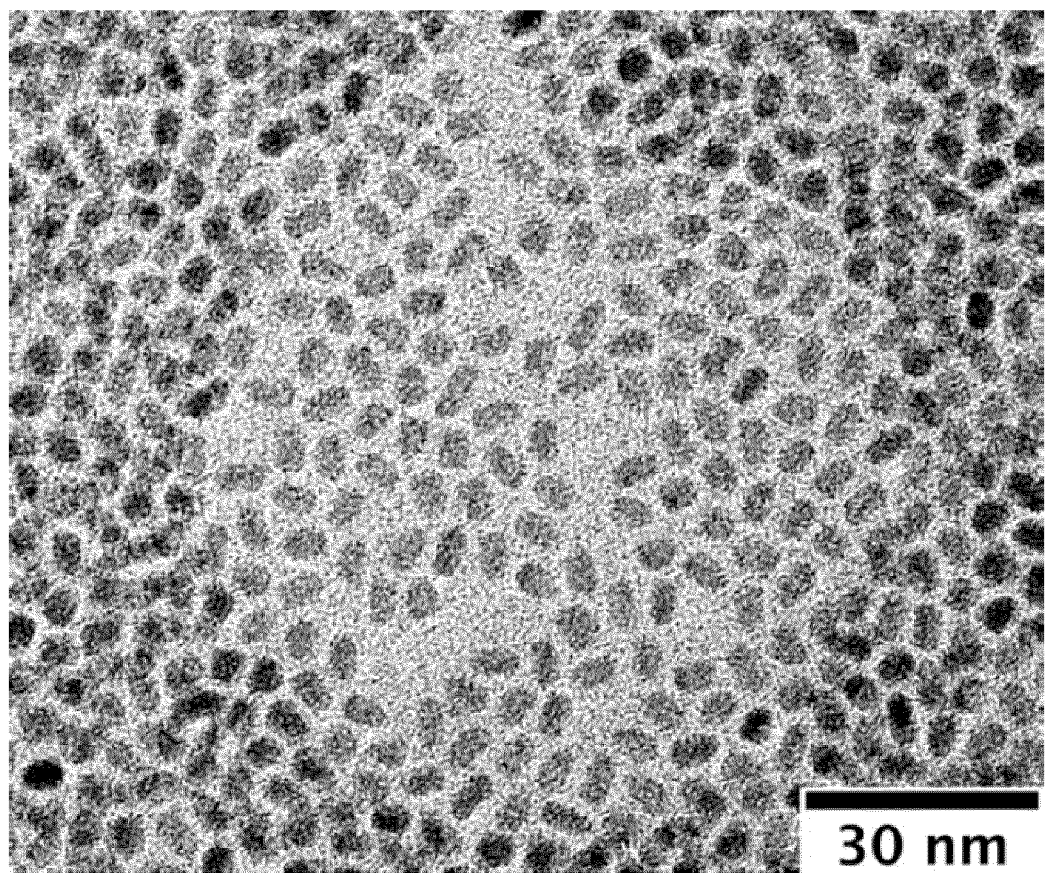
FIG. 10 shows a TEM image of CdSe QDs used as a PL and SERS reporters.
Figures 11A, 11B, 11C:
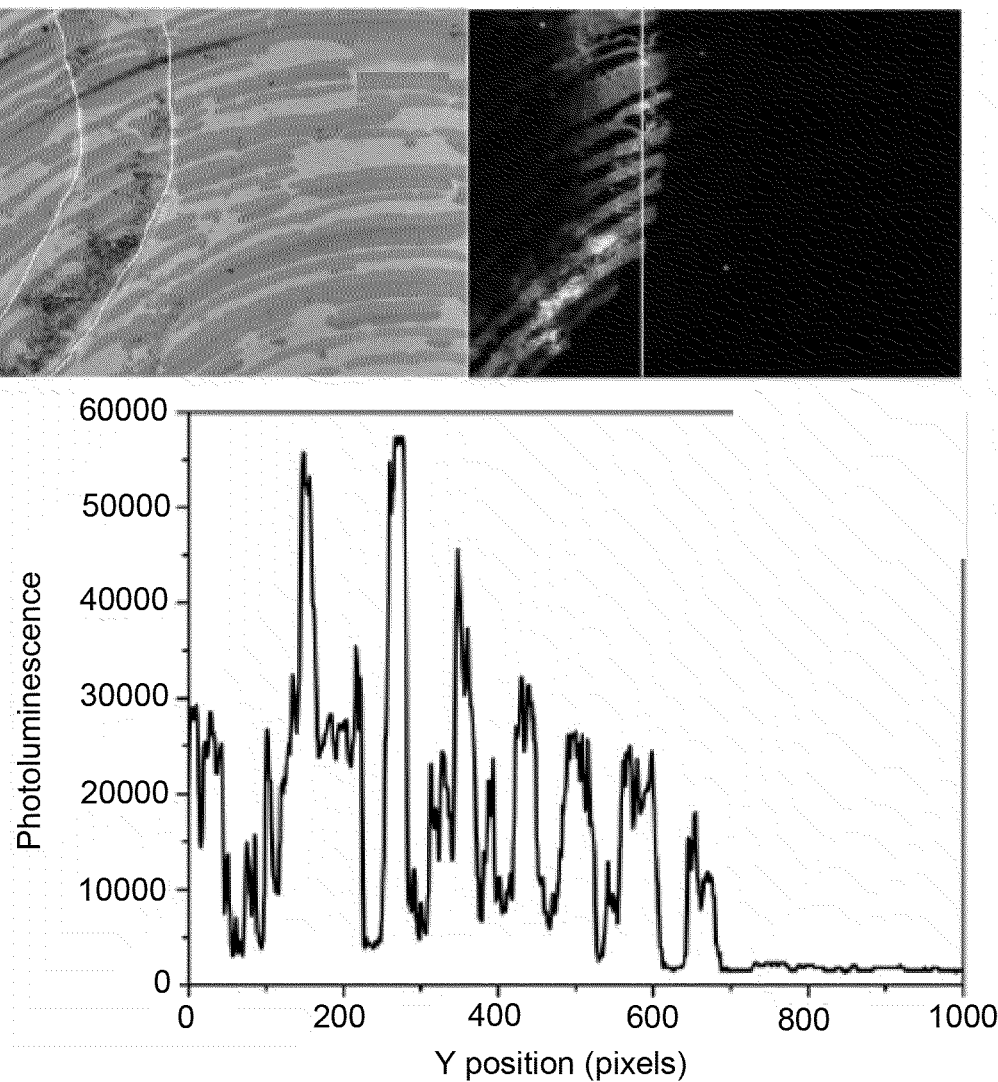
FIG. 11A shows an optical image of the "coffee-ring" deposit (between two white lines) of 5 nm CdSe QDs on the monolayer (light gray) and double-layer (dark gray) arrays of the Au nanoparticles and on bare Si (gray)
FIG. 11B shows the photoluminescence image of the same area observed under the UV illumination.
FIG. 11C shows the intensity profile along the white line shown in FIG. 11B which reveals 5 to 10 times PL enhancement by the Au nanoparticle arrays.

Electromagnetic hot spots have been prepared by others in the subnanometer gaps of large (≈50 nm) Au nanoparticle trimers and can provide a SERS enhancement factor of ≈$10^8$ in a wide range of frequencies near their plasmon resonances. This enhancement was strongly dependent on the gap size and was dominated by individual interparticle junctions. Multiple regular hot spots in our hcp structures offer a high average SERS sensitivity. The enhancement factor in different parts of our samples was estimated, where monolayer and double-layer nanoparticle assemblies and also bare substrate were distinguished by their contrast in reflected light. CdSe QDs (5 nm), which ensure good optical stability and low blinking and bleaching effect, were used as SERS reporters. An important advantage of these QDs is the possibility of resolving them with SEM so that their density and positions in our Au nanoparticle arrays can be directly imaged. Also, they show a good PL yield, which allows us to measure the PL enhancement factor in the nanoparticle arrays. FIG. 8A shows spectra of a dilute ($0.5 \times 10^4$ molL$^{-1}$) solution of CdSe QDs in toluene with well-resolved absorption and emission lines at 600 and 620 nm, respectively, indicative of a narrow size distribution (6%). TEM images (see FIG. 10) show that QDs have a shape of slightly prolate spheroids with an average diameter of 5 nm. The PL quantum yield of these particles has been estimated at 5%. To determine the PL enhancement, a 100 nM solution of CdSe QDs in toluene was drop-coated over the Au nanoparticle arrays, as shown in FIG. 8B. (Much lower QD concentrations yield no PL or Raman signal from the silicon surface, our reference for inferring enhancement factors, although we do obtain signals from our Au arrays.) The drying drop forms a "coffee-ring" pattern with increased density of particles and organic ligands at the periphery (stained region in FIG. 8B) on the Au monolayer (light gray), double layer (dark gray), and pure Si (gray). FIG. 8C shows the PL image of the CdSe QDs under UV illumination. Scans of the PL signal show up to 10 times higher intensity on the Au nanoparticle arrays (in both single- and double-layer areas) than in the bare Si stripes with the same QD density (see FIGS. 11A-11C). This value is ≈3-5 times higher than that previously reported for CdSe/ZnS core/shell QDs and CdSe QDs on disordered ≈15 nm Au nanoparticle assemblies with optimized dielectric spacer thickness. FIG. 8D shows the Raman spectra of CdSe QDs collected in different spots of the inset small box in FIG. 8B. The top curve is the SERS signal of the CdSe QDs on the Au monolayer, and the bottom curve is the signal on bare silicon substrate. Both spectra were collected under the same acquisition conditions in the spots shown by arrows in FIG. 8D. After extraction of the background, the Raman peak at 207 cm$^{-1}$ of the CdSe QDs deposited on the Au array is 500 times higher than that on silicon. This characteristic peak corresponds to the CdSe longitudinal optical phonon mode—LO(1). Also, the second harmonic of this vibrational mode, −2LO(1), near 414 cm$^{-1}$ is clearly seen on Au nanoparticles but is not resolved for QDs on silicon. The QD Raman peaks in FIG. 8D are more pronounced than those measured in commercial plasmonic arrays of inverted pyramids (Klarite substrates) excited at the same 514 nm wavelength. The 2D Raman scan image at 207 cm$^{-1}$ (inset in FIG. 8D) clearly visualizes the enhancement of the SERS signal on the Au nanoparticle arrays. The high-resolution SEM images in FIG. 8E reveal the same areal density of QDs on bare Si and on the Au arrays. We used SEM images of the QDs on the nanoparticles and electric field maps, such as shown in FIG. 6B, to determine the number of QDs situated in the highest local fields, since these QDs are likely to dominate the SERS signal. At 514 nm excitation the maximum electric fields are located approximately 10 nm away from the positions of the smallest gap between NPs. Such a symmetry of the 514 nm resonance, different from dipolar or quadrupolar modes of separated NPs, is very beneficial for our SERS experiment since 5 nm particles would not fit into the gap. The evaluation of this geometry yields that about 5% of the QDs are located in places of maximum electric field corresponding to a SERS gain of ≈$10^4$. Note the enhancement factor in question is associated with the volume of a hot spot, that is, it is not an average over all QDs, many of which are not in hot spots and not undergoing appreciable Raman scattering. This enhancement factor is a few orders of magnitude lower than those reported by others for clusters of colloidal metal NPs. However, in our case the number and positions of the QDs are directly visualized using high-resolution SEM, which eliminates the common problem of uncertainty in the analyte molecule density and location inherent for most experimental estimates of the SERS enhancement. Therefore, we obtain a reliable value of the enhancement factor, which is in a good agreement with the results of our FDTD simulations. For 514 nm they predict maximum amplification of the light intensity, $|E|^2$, ≈$10^2$ at ≈10 nm above the center of 1 nm gaps between nanoparticles (see FIG. 6B), which corresponds to a SERS enhancement of ≈$10^4$. For 830 nm excitation wavelength, located in the region of the strong resonance peak (FIG. 6A), we calculate ≈$10^3$ times larger SERS enhancement. However, even at 514 nm the high density of regular hot spots in our arrays significantly increases their practical sensitivity, thus allowing the detection of tiny amounts of chemical analytes.

Example III

Figure 12:
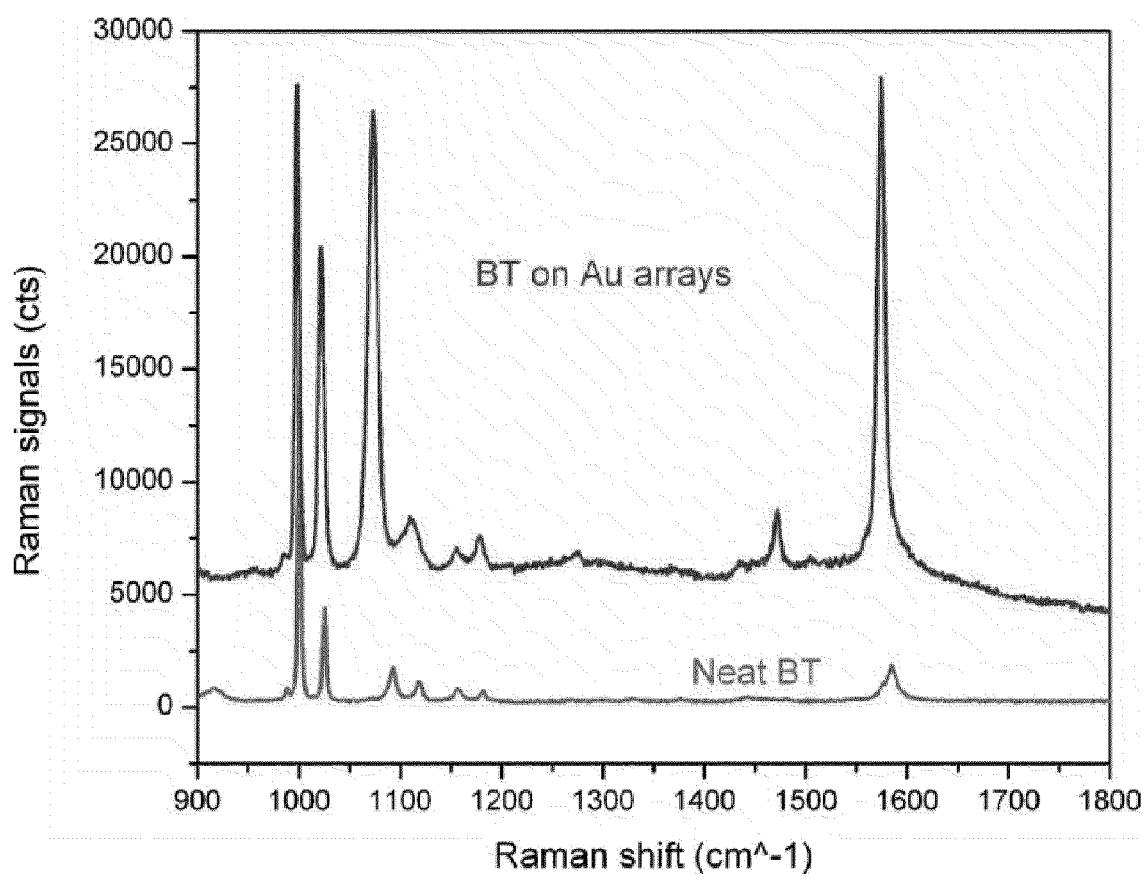
FIG. 12 shows Raman signals from a monolayer of Benzenethiol molecules deposited on 80 nm Au arrays (top line, 47 mW laser power, five acquisitions) and from neat BT (bottom line, 4.7 mW laser power, one acquisition)

To achieve larger SERS enhancement we covered our nanoparticle arrays with BT by soaking them for 12 h in 1 mM BT solution in ethanol and subsequently rinsing with pure ethanol. Such a procedure is known to form a continuous monolayer of BT molecules with $4.3-6.8 \times 10^{14}$ molecules per cm 2 surface coverage. The monolayer thickness of 0.6-0.8 nm estimated by X-ray photoelectron spectroscopy suggests good filling of the interparticle gaps. Also, for BT we used the largest excitation wavelength, 633 nm, available in our system, which provided higher light intensities in the gaps compared to 514 nm and a strong Raman signal, as shown in FIG. 12. No Raman peaks were seen from BT on flat glass or Au films. The enhancement factor was estimated from the comparison of this signal at the 1574 cm-1 line ($8a(a_1)$ C-C stretching mode of BT) at 47 μW laser power and the same line at 4.7 mW laser power from neat BT in a cuvette (bottom curve in FIG. 12). Traditional calculations of the number of molecules in appropriate excitation volumes and account of different excitation powers yields an average enhancement factor of ≈$10^6$. The single-molecule enhancement in the hot spots analogous to that determined for the QDs above is ≈$10^8$ if the hot spots are the main SERS source (see Example IV). In accordance with our FDTD calculations at 633 nm we considered that the large $E^2$ area is extended over an ≈5 nm spot around the minimum interparticle gap. Importantly, high-amplification hot spots are homogeneously distributed over the 1×1.5 μm$^2$ excitation area, which provides the stability and fidelity of the Raman signal.

A simple and cost-effective method is provided to self-assemble 80 nm Au colloidal nanoparticles into extended well-ordered structures. The large size of the nanoparticles and the long range order of arrays ensure high SERS and PL enhancement. Extinction spectra of our hcp Au nanoparticle crystals show strong interparticle coupling resulting in a distinct modification of their optical spectra and appearance of new resonance modes. These measurements are in a good agreement with the results of our FDTD simulations. The electromagnetic SERS enhancement factor of ≈$10^4$ (at 514 nm excitation) and the PL enhancement of ≈10 are determined using 5 nm CdSe QDs as reporters on the Au nanoparticle arrays. By depositing BT molecular analytes in the interparticle gaps and using a larger excitation wavelength, we obtain much larger enhancement factors of ≈$10^8$ associated with molecules in the hot spots. Ordered arrays of large noble-metal nanoparticles could become the basis for new high-fidelity SERS sensors and nanophotonic devices requiring strong local light amplification and a high density of hot spots.

Example IV

Au nanoparticle Self-Assembly methodology: Silicon wafers and microscope slides used as substrates were cleaned in oxygen plasma or in piranha solution (mixture of $H_2SO_4/H_2O_2$=3:1) at 120° C. for 10 min to remove organic contaminants and make the surface hydrophilic. Teflon ferrules (inner diameter ¼ inch) glued on the substrate with rubber cement were used to confine the nanoparticle solution. Au colloids (80 nm) were purchased from Ted Pella (original concentration $1.0 \times 10^{10}$ mL$^{-1}$) and concentrated to 1.0×10 11 mL$^{-1}$ in deionized water after 3× centrifugation at 1600 to 3000 rpm for 3 min in a 2-mL tube. Purified and concentrated Au nanoparticles (50 µL) were injected into the Teflon ferrule and covered with a glass slip to reduce evaporation. Usually, it took from 2 to 3 days to evaporate all the liquid. The position of the nanoparticle array growth front was determined with time and the speed determined for the monolayer and double-layer assembly as ≈0.1 and 0.03 µm s$^{-1}$, respectively.

Figure 13:
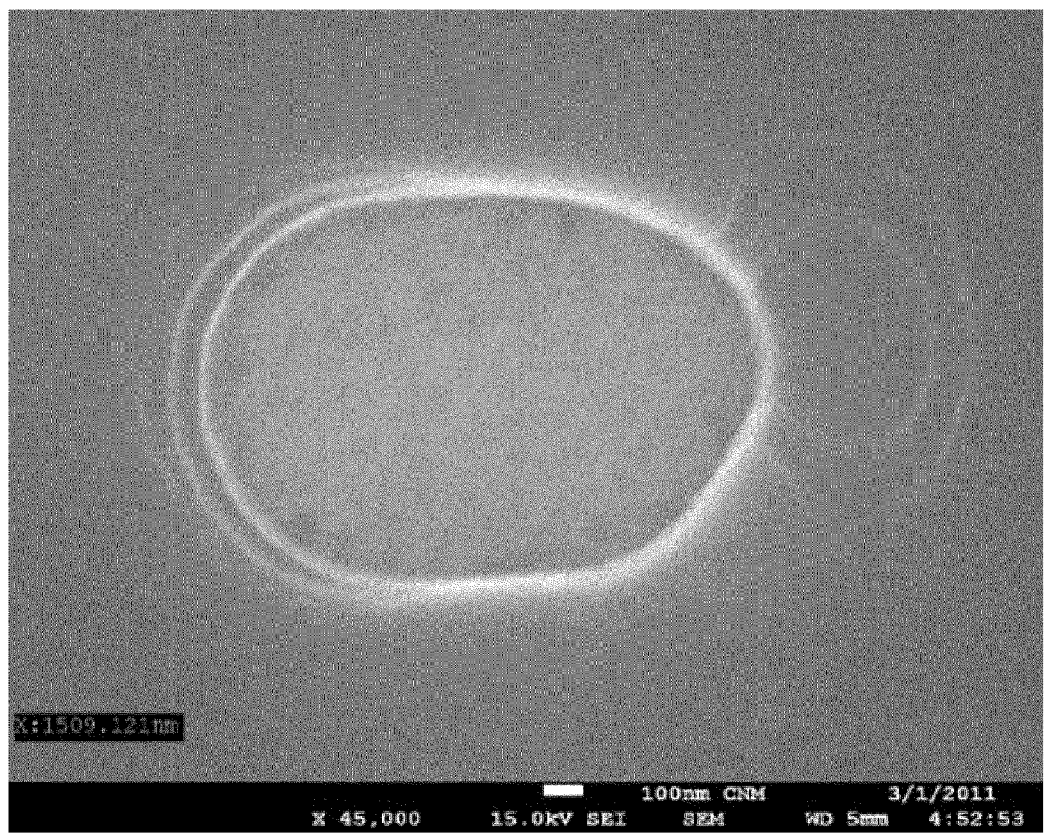
FIG. 13 shows an SEM image of an exposed beam spot in an SI805 resist with the focus size of a laser beam of about 1.0 µm×1.5 µm.

Extinction Measurement and Raman Characterization methodology: The UV-vis-near-infrared (NIR) extinction spectra at different points of the self-assembled Au arrays were measured using a modified microscope system and an Oriel MS257 spectrometer. A deuterium UV lamp and a wide-band halogen lamp were used for illumination. Raman spectra of CdSe QDs were measured using a Renishaw InVia Reflex Raman spectrometer with a 20× objective, 514 nm excitation wavelength, 80 µW power, ≈5 µm laser spot size, and 10 s integration time. Raman spectra of the BT molecules were collected in the same setup using a 50× objective at different powers of a 633 nm laser focused into a 1×1.5 µm 2 spot (see FIG. 13). For consistent and repeatable results, all Raman measurements from Au arrays were acquired five times at 10 s integration.

Calculation of SERS Enhancement for Benzenethiol methodology: The enhancement factor (EF) of a SERS substrate is determined as:

$$EF=(I_{sub}/N_{sub})/(I_{vol}/N_{vol})$$

where $I_{sub}$ and $I_{vol}$ are Raman signals from BT on the substrate and neat BT, respectively. $N_{sub}$ and $N_{vol}$ are the numbers of molecules in appropriate excitation volumes. The excitation volume of the neat BT is defined by the size of the focused laser spot. The transverse dimensions of the laser spot were found experimentally by focusing it in the Raman setup on ≈450-nm-thick S1805 photoresist with different exposures. The wavelength of the 633 nm laser and 50× objective were the same as for the acquisition of the neat BT spectra. After exposure for 10 s at 100, 5, 1, and 0.1% of the full 4.7 mW laser power, the resist was developed and exposed spots were measured using SEM. Going from small underexposed (0.1%) to large overexposed (5 and 100%) pits allowed us to find the optimum spot size of ≈1.0 µm×1.5 µm (FIG. S4), which is close to the 0.8 µm theoretical focus size for our 50× objective (numerical aperture, NA=0.75) at 633 nm wavelength. To determine the focus depth of our confocal microscope, we used an automated Z scan of the Raman system moving the cuvette with BT across the focal plane. The signal changed from zero when the focused beam was outside the cuvette to saturation when it was totally immersed in BT. From the $1/e^2$ profile of the scan we found the focal depth ≈10 µm. Therefore, the excitation volume=$(4\pi/3) \times 0.5 \times 0.75 \times 5$ $(\mu m)^3 \approx 7.8 \times 10^{-12}$ cm$^3$. Using the largest reported surface density of the BT monolayer on gold ($6.8 \times 10^{14}$ cm$^{-2}$) and the volume density of neat BT (1.0766 g cm$^{-3}$, or $5.855 \times 10^{21}$ cm$^{-3}$ with molecular weight 110.73 g mol$^{-1}$), we obtained $N_{sub} \approx 1.6 \times 10^7$ and $N_{vol} \approx 4.6 \times 10^{10}$. After subtraction of the background and normalization to the same laser power, the ratio of Raman signals at the 1574 cm$^{-1}$ line was ≈300. Thus, the average enhancement factor was ≈$0.9 \times 10^6$. Our FDTD calculations showed that at 633 nm excitation the maximum electromagnetic field is confined in 5 nm spots around the smallest interparticle gaps and for the linear light polarization there is only one hot spot per particle. Accounting for the fact that the main Raman signal comes from BT molecules in the hot spots and estimating the number of molecules over these hot spots in the laser focus, the number of BT molecules located in the hot spot was only ≈$6.3 \times 10^4$, which corresponded to a maximum of SERS EF ≈$2.2 \times 10^8$.

The methods, systems and articles of manufacture provide greatly enhanced Raman spectrometry for many commercial applications. The described Raman substrates can be used, for example, in bio-chemical methodologies, medical applications, pharmaceutical uses, homeland security applications for detection and analysis of tiny amounts of inorganic and organic components, virus detection and analysis, explosives, detection and analysis, and diagnosis of various diseases. The light amplification techniques can be extended to light harvesting, solid state lighting and in photonic chips.

The foregoing description of embodiments of the present invention has been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments, and with various modifications, as are suited to the particular use contemplated.

What is claimed is:

1. A method of light amplification for surface enhanced Raman spectroscopy, comprising the steps of,
    providing a source for input light;
    providing a continuous layer grating having grooves therein;
    disposing a nanoparticle array directly in contact with the grooves of the grating, the grating having a period for the grooves based on different parameters of the nanoparticle array and the grating; and
    arranging the nanoparticle array and selecting nanoparticles of different selected characteristics such that resonances of the grating and the nanoparticle array provide a same tuned frequency, thereby enabling scaled amplification of the input light to the nanoparticle array disposed in the grating to provide an amplified out-light signal for performing surface enhanced Raman spectroscopy.

2. The method as defined in claim 1 wherein the steps of arranging the nanoparticles of different selected characteristics includes at least one of selecting different particle size and shape to thereby provide high interparticle light fields and increase density of interparticle resonance hot spots.

3. The method as defined in claim 1 wherein pitch of the grating includes a dielectric metal surface disposed on a substrate.

4. The method as defined in claim 1 wherein the different parameters of the nanoparticle array are selected from the group consisting of particle size, particle material, particle shape, spacing of the nanoparticles and characteristics of gaps between the nanoparticles.

5. The method as defined in claim 4 wherein the characteristics of the interparticle gap is selected from the group of physical properties and chemical properties.

6. The method as defined in claim 4 wherein the particle size is selected from the group of (a) different size, but all particles being of same size and (b) different mixed particle sizes.

7. The method as defined in claim 3 wherein the metal surface is selected from the group consisting of Ag and Au.

8. The method as defined in claim 3 wherein the substrate is selected from the group of $SiO_2$ and Si.

9. The method as defined in claim 3 further including a patterned layer of HSQ comprising the grating.

10. The method as defined in claim 1 wherein the nanoparticles include a coating.

11. The method as defined in claim 1 wherein the nanoparticles include a metal nanoshell.

12. The method as defined in claim 1 further including the step of selecting the parameters of the nanoparticle array to introduce light red-shift to expand resonance amplification.

13. A method of light amplification for surface enhanced Raman spectroscopy, comprising the steps of,
providing a source for input light;
providing a substrate and a continuous layer grating having grooves therein; and
arranging the nanoparticles with different selectable parameters which nanoparticles are in direct contact with the grating to cause a density increase of interparticle resonance hot spots and to resonate the grating, the substrate and the nanoparticles all at the same frequency, thereby providing an initial amplification of the input light for an output light signal and Raman spectroscopy therein.

14. The method as defined in claim 13 wherein pitch of grating comprises a dielectric metal surface disposed on a substrate.

15. The method as defined in claim 13 wherein the different nanoparticle parameters are selected from the group consisting of particle size, particle material, particle shape, spacing of the nanoparticles and characteristics of gaps between the nanoparticles.

16. A system for light amplification for surface enhanced Raman spectroscopy, comprising the steps of,
a source for input light;
a substrate with a continuous layer grating thereon and having grooves therein;
a nanoparticle array disposed directly in contact with the grooves of the grating, the grating having a period for the grooves based on different parameters of the nanoparticle array and the grating; and
the nanoparticles having different selected characteristics such that resonances of the grating, the substrate and the nanoparticle array provide a same tuned frequency, thereby enabling scaled amplification of the input light to the nanoparticle array disposed in the grating to provide an amplified out-light signal for performing surface enhanced Raman spectroscopy.

17. The system as defined in claim 16 wherein the nanoparticle array and the different selected characteristics of nanoparticles of the array have resonances at the same tuned frequency, thereby enabling scaled amplification of the input light such that an output light signal is amplified by an exponential product of contributing features of the system.

18. The system as defined in claim 16 wherein the parameters of the nanoparticle array are selected from the group consisting of particle size, particle material, particle shape, spacing of the nanoparticles and nature of gaps between the nanoparticles.

19. The system as defined in claim 16 wherein the different nanoparticle array parameters are selected from the group of interparticle gap physical properties, interparticle chemical properties, particles of same size but selectable in size, particles of mixed size, a mixture of metal material, particles having a coating and a layered nanoparticle.

20. The system as defined in claim 16 wherein the nanoparticle array has a structure arranged to increase density of interparticle resonance hot spots, thereby providing enhanced initial amplification of the input light.

* * * * *